(12) United States Patent
Knaeble

(10) Patent No.: US 10,676,410 B2
(45) Date of Patent: Jun. 9, 2020

(54) SYSTEMS AND PROCESSES FOR ALKANE AROMATIZATION

(71) Applicant: ExxonMobil Chemical Patents Inc., Baytown, TX (US)

(72) Inventor: William J. Knaeble, Bridgewater, NJ (US)

(73) Assignee: ExxonMobil Chemical Patents Inc., Baytown, TX (US)

(*) Notice: Subject to any disclaimer, the term of this patent is extended or adjusted under 35 U.S.C. 154(b) by 20 days.

(21) Appl. No.: 15/960,221

(22) Filed: Apr. 23, 2018

(65) Prior Publication Data
US 2018/0370870 A1    Dec. 27, 2018

Related U.S. Application Data

(60) Provisional application No. 62/523,468, filed on Jun. 22, 2017.

(51) Int. Cl.
C07C 2/42    (2006.01)
C07C 2/66    (2006.01)

(52) U.S. Cl.
CPC .......... C07C 2/42 (2013.01); C07C 2/66 (2013.01); C07C 2529/40 (2013.01)

(58) Field of Classification Search
CPC .............. C07C 2/00; C07C 2/42; C07C 2/66
See application file for complete search history.

(56) References Cited

U.S. PATENT DOCUMENTS

| | | | |
|---|---|---|---|
| 3,702,886 A | 11/1972 | Argauer et al. | |
| 3,709,979 A | 1/1973 | Chu | |
| 3,832,449 A | 8/1974 | Rosinski et al. | |
| 4,016,218 A | 4/1977 | Haag et al. | |
| 4,016,245 A | 4/1977 | Plank et al. | |
| 4,046,859 A | 9/1977 | Plank et al. | |
| 4,076,842 A | 2/1978 | Plank et al. | |
| 4,082,805 A | 4/1978 | Kaeding | |
| RE29,948 E | 3/1979 | Dwyer et al. | |
| 4,229,424 A | 10/1980 | Kokotailo | |
| 4,234,231 A | 11/1980 | Yan | |
| 4,350,835 A * | 9/1982 | Chester | B01J 29/40 502/61 |
| 4,556,477 A | 12/1985 | Dwyer | |
| 4,640,826 A | 2/1987 | Williams et al. | |
| 4,642,402 A * | 2/1987 | Jensen | C07C 2/00 585/411 |
| 4,873,067 A | 10/1989 | Valyocsik et al. | |
| 8,692,043 B2 | 4/2014 | Lauritzen et al. | |
| 2004/0015027 A1* | 1/2004 | Iaccino | C07C 2/66 585/448 |
| 2016/0083313 A1* | 3/2016 | Negiz | C07C 2/00 585/313 |

* cited by examiner

Primary Examiner — In Suk C Bullock
Assistant Examiner — Alyssa L Cepluch

(57) ABSTRACT

Embodiments disclosed herein related to processes and systems for alkane aromatization. In some embodiments, the process includes merging a benzene-containing stream into an ethane containing stream to form a feed stream. The feed stream has at least 5 wt. % benzene based on the total weight of the feed stream. In addition, the process includes contacting the feed stream with an aromatization catalyst to produce an effluent stream comprising $C_{7+}$ aromatic hydrocarbons. Less than 5 wt. % net benzene is produced during the contacting, based on a total weight of the feed stream.

17 Claims, 3 Drawing Sheets

SYSTEMS AND PROCESSES FOR ALKANE AROMATIZATION

CROSS-REFERENCE OF RELATED APPLICATIONS

This application claims the benefit of U.S. Provisional Patent Application Ser. No. 62/523,468, filed Jun. 22, 2017, and entitled "Systems and Processes for Alkane Aromatization," which is herein incorporated by reference in its entirety.

TECHNICAL FIELD

This disclosure generally relates to the conversion of alkane-containing feed streams. More particularly, this disclosure relates to the production of aromatic hydrocarbons from alkane-containing feed streams.

BACKGROUND

Natural gas has become a relatively inexpensive and abundant feedstock that is available for conversion and economic upgrading. Typically, natural gas streams may contain up to 50 vol. % or more $C_{2+}$ alkanes (e.g., ethane, propane, butane, etc.), which can be converted to aromatic rich stream (e.g., aromatic-rich naphtha). However, such aromatic-rich streams typically contain a relatively large amount of benzene. Due to regulations that limit the amount of benzene allowed in motor gasoline and other products, aromatic liquid streams must typically be processed to remove excessive amounts benzene before such streams may be utilized in a gasoline product (e.g., a MOGAS pool). Additionally, a lower benzene content in produced aromatic-rich streams may be more efficiently processed by other xylene production processes (e.g., toluene methylation, crystallization, adsorption, etc.). Thus, it would be desirable to produce an aromatic-rich product stream from a $C_{2+}$ alkane aromatization process that includes a relatively small amount of benzene.

BRIEF SUMMARY

Embodiments disclosed herein are directed to systems and processes for producing aromatic hydrocarbons from an alkane-containing feed stream (e.g., ethane), while minimizing or eliminating the amount of produced benzene in the aromatization reactor effluent. In at least some embodiments, the reduction in benzene produced in the aromatization process (i.e., net benzene) is achieved by co-feeding or recycling benzene into the aromatization reactor along with the alkane-containing feed stream. It has unexpectedly been discovered that providing this additional benzene to the aromatization reactor causes additional reactions that reduce the resulting amount of benzene ultimately produced therefrom.

For example, some embodiments disclosed herein are directed to a process including merging a benzene-containing stream into an ethane containing stream to form a feed stream. The feed stream has at least 5 wt. % benzene based on the total weight of the feed stream. In addition, the process includes contacting the feed stream with an aromatization catalyst to produce an effluent stream comprising $C_{7+}$ aromatic hydrocarbons, wherein less than 5 wt. % net benzene is produced during the contacting, based on a total weight of the feed stream.

Other embodiments disclosed herein are directed to a process including flowing a feed stream to an aromatization reactor. The feed stream comprises at least 50 wt. % ethane based on the total weight of the feed stream. In addition, the process includes contacting the feed stream with an aromatization catalysts to produce an effluent stream comprising $C_{7+}$ aromatic hydrocarbons. Less than 5 wt. % net benzene is produced during the contacting, based on a total weight of the feed stream. Further, the process includes separating a $C_2$-$C_6$ aromatic hydrocarbon-containing stream from the effluent stream, and recycling the $C_2$-$C_6$ aromatic hydrocarbon-containing stream to the aromatization reactor so that at least 5 wt. % of benzene is provided to the aromatization reactor, based on the total weight of the feed stream and the $C_2$-$C_6$ aromatic hydrocarbon stream.

DETAILED DESCRIPTION

Figure 1:
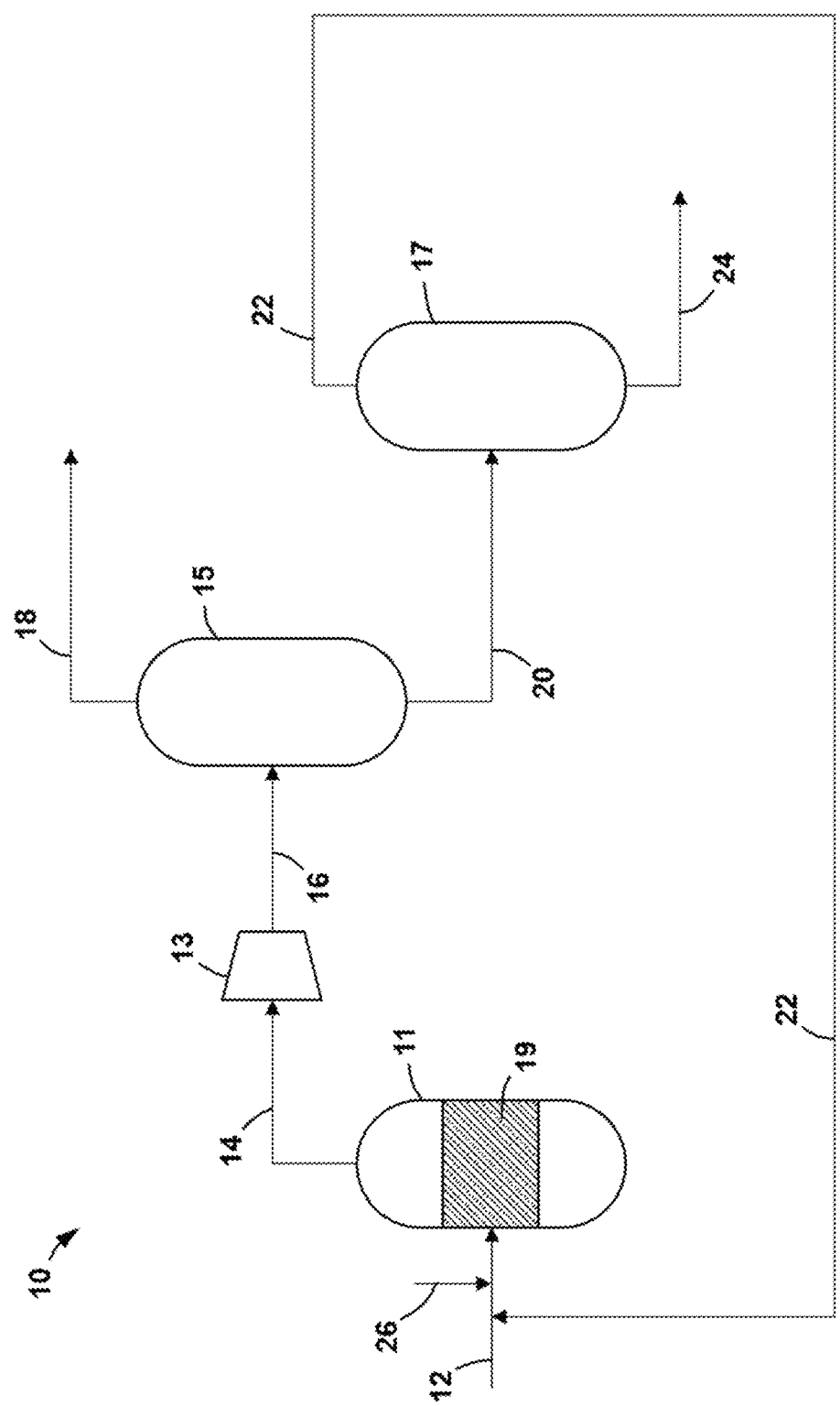
FIG. 1 is a flow diagram of an embodiment of a process for producing an aromatic hydrocarbon-containing product stream from an alkane-containing feedstock in accordance with at least some embodiments disclosed herein.

The following discussion is directed to various embodiments. However, it should be appreciated that the embodiments disclosed herein have broad application, and that the discussion of any embodiment is meant only to be exemplary of that embodiment, and not intended to suggest that the scope of the disclosure, including the claims, is limited to that embodiment. In the drawings, certain features and components herein may be shown exaggerated in scale or in somewhat schematic form and some details of conventional elements may not be shown in interest of clarity and conciseness. All documents described herein are incorporated by reference, including any priority documents and/or testing procedures, to the extent they are not inconsistent with this text. When numerical lower limits and numerical upper limits are listed herein, ranges from any lower limit to any upper limit are contemplated. As used herein, the term "rich" when used in phrases such as "X-rich" or "rich in X" means, with respect to an outgoing stream obtained from a device, that the stream comprises material X at a concentration higher than in the feed material fed to the same device from which the stream is derived. As used herein, the words "about," "approximately," "substantially," around," and the like mean +/−10%.

Embodiments disclosed herein are generally directed to processes and systems for producing aromatic hydrocarbons from alkane-containing feed stream (e.g., natural gas, refinery streams, etc.). In at least some embodiments, the alkane-containing feed stream comprises a majority fraction of ethane (i.e., greater than 50 wt. % ethane based on the total weight of the alkane-containing feed stream). The catalyst utilized for the conversion of ethane to aromatic hydrocarbons may be any suitable catalyst known for performing such a conversion. For example, in some embodiments, the catalyst utilized herein for the aromatization reaction comprises a molecular sieve such as an aluminosilicate and a metal function.

In particular, in at least some embodiments, the catalyst comprises ≥25 wt. % of a molecular sieve component and ≥0.05 wt. % of a dehydrogenation component, where these weight percentages are relative to the total weight of the catalyst. In some embodiments, the molecular sieve component comprises ≥90 wt. % of one or more of ZSM-5, ZSM-11, ZSM-12, ZSM-21, ZSM-22, ZSM-23, ZSM-35, ZSM-38, ZSM-48 ZSM-50, ZSM-57, MCM-22, and MCM-68, including mixtures and intermediates thereof (e.g., a ZSM-5/ZSM-11 admixture). ZSM-5 is described in U.S. Pat. No. 3,702,886 and Re. 29,948. ZSM-11 is described in U.S. Pat. No. 3,709,979. A ZSM-5/ZSM-11 intermediate structure is described in U.S. Pat. No. 4,229,424. ZSM-12 is described in U.S. Pat. No. 3,832,449. ZSM-21 is described U.S. Pat. No. 4,082,805. ZSM-22 is described in U.S. Pat. No. 4,556,477. ZSM-23 is described in U.S. Pat. No. 4,076,842. ZSM-35 is described in U.S. Pat. No. 4,016,245. ZSM-38 is described in U.S. Pat. No. 4,046,859. ZSM-48 is described in U.S. Pat. No. 4,234,231. ZSM-50 is described in U.S. Pat. No. 4,640,826. ZSM-57 is described in U.S. Pat. No. 4,873,067. Each of the above referenced U.S. patents are hereby incorporated herein by reference.

As previously described, the catalyst utilized for the conversion of ethane to aromatic hydrocarbons in the embodiments described herein may comprise a dehydrogenation component. In some embodiments, the dehydrogenation component comprises ≥90 wt. % of one or more of Ga, Zn, Cu, Re, Mo, W, La, Fe, Ag, Pt, and Pd.

Additionally, or alternatively, some molecular sieves useful here are described or characterized by a Constrain Index of about 1 to about 12. Constraint Index is determined as described in U.S. Pat. No. 4,016,218, which is incorporated herein by references for the details of the method.

Zeolite catalyst for use in embodiments disclosed herein may be converted from natural zeolites by various activation procedures and other treatments such as base exchange, steaming, alumina extraction and calcination, or combinations thereof. Examples of natural minerals which may be so treated include ferrierite, brewsterite, stilbite, dachiardite, epistilbite, heulandite, and clinoptilolite.

The catalysts described herein may be used in an acidic or hydrogen form or they may be base exchanged or impregnated to contain ammonium or a metal cation complement. It is desirable to calcine the catalyst after base exchange. The metal cations that may be present include any of the cations of the metals of Groups 1, 2, or 8-14 of the IUPAC (International Union of Pure and Applied Chemistry) Periodic Table and mixtures thereof.

In at least some embodiments, the catalysts used herein are selected from those also having a crystal framework density, in the dry hydrogen form, of not substantially below about 1.6 grams per cubic centimeter. More particularly, at least some embodiments include a zeolite aromatization catalyst having a constraint index as defined above of about 1 to about 12, and a silica to alumina ratio of at least about 5.

When synthesized in the alkali metal form, zeolites useful for embodiments disclosed herein may be conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 50 percent by weight of the original alkali metal contained therein usually 0.5 wt. % or less may be used. Thus, as previously described, the original alkali metal of the zeolite may be replaced by ion exchange with other suitable ions of Groups 1, 2, and 8-14 of the IUPAC Periodic Table including, by way of example, zinc, copper or platinum groups metals and combinations thereof. In at least some embodiments a zinc-copper mixture may be preferred. The amount of metal so utilized can vary between wide limits, depending, interalia, or intended reaction conditions, etc. However, catalysts of the at least some embodiments disclosed herein usually contain from about 0.01 to about 30 wt. % of the metal (or metals) described above based on the total weight of the catalyst. In other embodiments, from about 0.5 to about 10 wt. % metal is present in the catalyst.

Although it is not required, the catalyst utilized herein optionally includes a binder (e.g., matrix) but in an amount typically <50 wt. % based on the weight of the catalyst, e.g., ≤30 wt. %, such as ≤20 wt. %, or ≤15 wt. %, or ≤10 wt. %, or ≤1 wt. %. When used, the binder can include inorganic material, e.g., clays and/or inorganic oxides. Suitable inorganic binders include alumina, silica, silica-alumina, titania, zirconia, magnesia, tungsten oxide, ceria, niobia, and mixtures of two or more thereof. The matrix can include naturally occurring materials and/or materials in the form of gelatinous precipitates or gels including mixtures of silica and metal oxides. Clays may also be included with the oxide type binders to modify the mechanical properties of the catalyst or to assist in its manufacture. Optionally, the binder may include one or more substantially inactive materials, e.g., diluent to control the amount of conversion so that products may be obtained economically and orderly without employing other means for controlling the rate of reaction. These materials may be incorporated into naturally occurring clays, e.g., bentonite and kaolin, to improve thermal and strength properties (e.g., crush strength) of the catalyst under catalytic conversion conditions. The binder may include other active materials, such as synthetic or naturally occurring aluminosilicate.

Referring now to FIG. 1, an embodiment of a process 10 for producing an aromatic hydrocarbon-containing product stream from a light alkane feedstock is shown. Initially, a feed stream 12 that comprises $C_{2+}$ alkanes (e.g., paraffins and/or olefins) is provided to an aromatization reactor 11. In at least some embodiments, feed stream 12 comprises ethane in an amount ≥1 wt. %, e.g., ≥5 wt. %, such as ≥10 wt. % based on the total weight of feed stream 12. Suitable feedstock include those containing a majority fraction of ethane, e.g., >50 wt. % ethane, such as ≥75 wt. %, or ≥90 wt. %, or ≥95 wt. %. For example, the feed stream 12 can comprise an amount of ethane in the range of from 1 wt. % to 100 wt. %, such as 5 wt. % to 95 wt. %, or 10 wt. % to 90 wt. % based on the total weight of feed stream. One representative feed stream 12 comprises (i) ≥10 wt. % ethane, or ≥50 wt. %, or ≥90 wt. %, such as in the range of from 10 wt. % to 99.5 wt. % ethane, with ≥95 wt. % of the balance of the feed stream comprising one or more of methane, propane, and butanes. Feed stream 12 may be derived from any suitable source, such as, for example, a natural gas pipeline, a naphtha hydro-treater, a cracking unit, a hydro-processing unit, etc.

Feed stream 12 is flowed to aromatization reactor 11 (which may comprise one or more vessels, chambers, etc.) and contacted with an aromatization catalyst 19 under appropriate reaction conditions (discussed below) to convert at least some of the ethane in feed stream 12 into aromatic hydrocarbons that are emitted in a reactor effluent stream 14.

In addition, in at least some embodiments, an additional stream 26 containing $C_6$-$C_7$ aromatic hydrocarbons (i.e., benzene and/or toluene) is co-fed into reaction chamber 11 along with feed stream 12. The stream 26 may comprise ≥50 wt. % $C_6$-$C_7$ aromatic hydrocarbons, e.g., >60 wt. %, >75 wt. %, >80 wt. %, >95 wt. % based on the total weight of stream 26. In these embodiments, the portion of stream 26 comprised of $C_6$-$C_7$ aromatic hydrocarbons may completely comprise benzene, may completely comprise toluene, or may comprise a mixture of benzene and toluene. In at least some embodiments, stream 26 may comprise at least 1 wt. % benzene, such as, e.g., >10 wt. %, >20 wt. %, >40 wt. %, >80 wt. %, >99 wt. %. In addition, in at least some embodiments, stream 26 may comprise at least 1 wt. % toluene, such as, e.g., >10 wt. %, >20 wt. %, >40 wt. %, >80 wt. %, >99 wt. %. Each of the weight percentages above are based on the total weight of stream 26. Thus, in at least some embodiments, stream 26 may comprise a majority fraction of benzene. In addition, stream 26 may be derived from any suitable source, such as, for example, a distillation tower (e.g., a crude distillation tower), a trans alkylation unit, a naphtha reformer, etc.

The aromatization catalyst 19 may be any suitable catalyst or catalyst system for converting alkane-containing feed streams (or at least some portion thereof) into aromatic-rich effluent streams (e.g., effluent stream 14). For example, in some embodiments, the aromatization catalyst may comprise a molecular sieve, such as a zeolite catalyst according to those previously described above. The catalyst bed may be one or more of a fixed bed, a moving bed, or fluidized bed. Conventional fixed, moving, and/or fluidized beds may be used in one or more of the reaction zones, but the embodiments disclosed herein are not limited thereto. Although the catalyst can be present in the reaction zone in the form of a fluidized particulate, the process can alternatively or in-addition be carried out with the catalyst in the form of a plurality of catalytic solid bodies, e.g., macrostructures such as extrudates, pellets, etc.

The reaction conditions within reactor 11 may include any suitable conditions for converting at least some of the lower alkanes (e.g., ethane) in to aromatic hydrocarbons in the presence of one of more of the catalyst described herein (e.g., aromatization catalyst 19). For example, in some embodiments, the process conditions within reactor 11 include a temperature in the range of from 400° C. to 750° C., more preferably from 400° C. to 670° C., and more preferably from 500° C. to 650° C. In addition, the process conditions within reaction chamber include a pressure in the range of from 35 kPaa (5 psia) to 2200 kPaa (319 psia), more preferably from about 70 kPaa (10 psia) to about 2070 kPaa (300 psia), and still more preferably from 138 kPaa (20 psia) to 522 kPaa (80 psia). Further, the process conditions within reaction chamber include a weight hourly space velocity (WHSV) ≥0.1 $hr^{-1}$, such as a WHSV of 0.1 $hr^{-1}$ to 20 $hr^{-1}$, more preferably from 0.1 $hr^{-1}$ to 10 $hr^{-1}$.

In at least some embodiments, reactor effluent stream 14 comprises methane (e.g., between 1 and 10 wt. %), ethane (e.g., between 50 and 90 wt. %), benzene (e.g., between 5 and 25 wt. %), toluene (e.g., between 5 and 25 wt. %), other $C_{8+}$ aromatic hydrocarbons (e.g., between 5 and 25 wt. %), olefins (e.g., between 0.1 and 10 wt. %), and $C_{3+}$ paraffins (e.g., between 0.1 to 10 wt. %).

The reactor effluent stream 14 is then flowed (optionally aided by pump or compressor 13 to convert to a compressed stream 16) to a first separation unit 15, which may comprise a single or multiple separation reactors, columns, etc. In this embodiment first separation unit 15 is configured to separate the reactor effluent stream 14 into a lights stream 18 comprising $C_1$ hydrocarbons, hydrogen gas ($H_2$), and a bottoms stream 20 comprising $C_{2+}$ hydrocarbons. Thereafter, the bottoms stream 20 is routed to a second separation unit 17 which may also comprise a single or multiple separation reactors, columns, etc. In this embodiment, second separation unit 17 is configured to separate the bottoms stream 20 into another bottoms stream 24 comprising $C_{7+}$ hydrocarbons, including $C_{7+}$ aromatic hydrocarbons (e.g., toluene, xylenes, etc.), and another light stream 22 comprising $C_2$-$C_6$ hydrocarbons, including $C_2$-$C_6$ aromatic hydrocarbons.

Bottoms stream 24 may include a substantial fraction of toluene, xylenes, and/or heavier aromatic hydrocarbons (e.g., $C_{9+}$ aromatic hydrocarbons). As a result, stream 24 may be fed to another unit or process in order to facilitate the production and/or isolation of other valuable products, such as, for example, para-xylene. In particular, bottoms stream 24 may be provided to a para-xylene production unit (e.g., toluene methylation unit, crystallization, selective adsorption, or combinations thereof).

In at least some embodiments, light stream 22 may comprise at least 1 wt. % benzene, such as, for example, from about 1 to about 20 wt. %, from about 5 to about 15 wt. %, or even from about 10 to about 15 wt. %. Each of the weight percentages above are based on the total weight of stream 22. In at least some embodiments, lights stream 22 may include a majority fraction of benzene (i.e., greater than 50 wt. % benzene based on the total weight of stream 22).

Referring still to FIG. 1, in this embodiment at least some or all of light stream 22 is recycled to reactor 11. Specifically, as shown in FIG. 1, light stream 22 is recycled back to and merged with feed stream 12 upstream of reactor 11 so that stream 12 includes at an increased amount of benzene. Alternatively or additionally, the additional benzene to feed stream 12 is provided via stream 26, previously described. In embodiments where benzene production is to be minimized or prevented entirely, light stream 22 and/or stream 26 may be configured (e.g., in composition, flow rate, etc.) so that when streams 22 and/or 26 are mixed with feed stream 12, the total stream to reactor 11 (which may also be referred to herein as a "feed stream" or a "merged stream") includes from 5 to 30 wt. % benzene, or more preferably from 10 to 20 wt. % benzene, based on the total weight of the stream provided to reactor 11. In these embodiments, the amount of benzene produced in reactor 11 (i.e., the amount of net produced benzene) may be less than 5 wt. %, less than 2 wt. %, less than 1 wt. %, etc., based on the total weight of stream 14. In some embodiments, effluent stream 14 includes a lower amount of benzene than that total feed to reactor 11 (e.g., so that the net benzene produced from reactor 11 is less than 0 wt. %).

In addition, it should be appreciated that light stream 22 and/or stream 26 may be merged with feed stream 12 to create a "merged stream" that is fed to reactor 11. As used herein, the terms "merge," "merging," "merged," apply to both when streams 22 and/or 26 are combined with feed stream 12 upstream of reactor 11 and when stream 22 and/or 26 are combined with feed stream 12 within reactor 11.

Without being limited to this or any other theory, the concentration of benzene (and/or toluene) in the reactor effluent 14 is set, in part, by thermodynamic equilibrium among the aromatic hydrocarbons in the effluent. Therefore co-feeding benzene (and/or toluene) is believed to cause a decrease in the net production of benzene from reactor 11 due to a shift in the overall aromatic hydrocarbons toward equilibrium in light of this increased amount of benzene. In addition, benzene (and/or toluene) may form heavier aromatic hydrocarbons in reactor 11 by undergoing alkylation reactions with adsorbed olefins at Brønsted acid sites. In addition, benzene (and/or toluene may adsorb at such acid sites, thereby decreasing the number ethane molecules that may adsorb at such acid sited so that there is an overall decrease in ethane conversion. Further, the alkylation reactions of benzene (and/or toluene) with methyl fragments at Brønsted acid sites decreases methane production by decreasing the number of methyl fragments at such acid sites that may otherwise lead to methane production via hydride transfer reactions with gas phase alkanes Thus, by providing additional benzene to the feed stream to aromatization reactor, ethane in feed stream 12 may be effectively converted to aromatics, and the benzene fraction produced from this reaction may be decreased, minimized, or altogether eliminated. As described above, the additional benzene may be derived from recycling a benzene containing stream (e.g., stream 22) back to aromatization reactor 11 and/or by including an additional benzene-containing stream from another process or unit (e.g., stream 26). Accordingly, as a result of the reduced production of benzene in reactor 11, the product stream(s) from process (e.g., stream 24) may be more readily useful and valuable for subsequent processing operations (e.g., gasoline or para-xylene production operations). In particular, due to the decreased production of benzene in reactor 11, the weight percentage of $C_{7+}$ aromatic hydrocarbons (particularly toluene and xylenes) produced from ethane in reactor 11 may be increased so that subsequent processing operations (e.g., para-xylene production and isolation via crystallization, selective adsorption, trans alkylation, etc.) may be carried out with greater efficiency. For example, in some embodiments, as a result of the co-feeding a benzene-containing stream (e.g., via stream 22 and/or stream 26) to reactor 11, about 40% to 90% (by volume) or more of ethane provided to reactor 11 is converted to $C_{7+}$ aromatic hydrocarbons.

Figure 2:
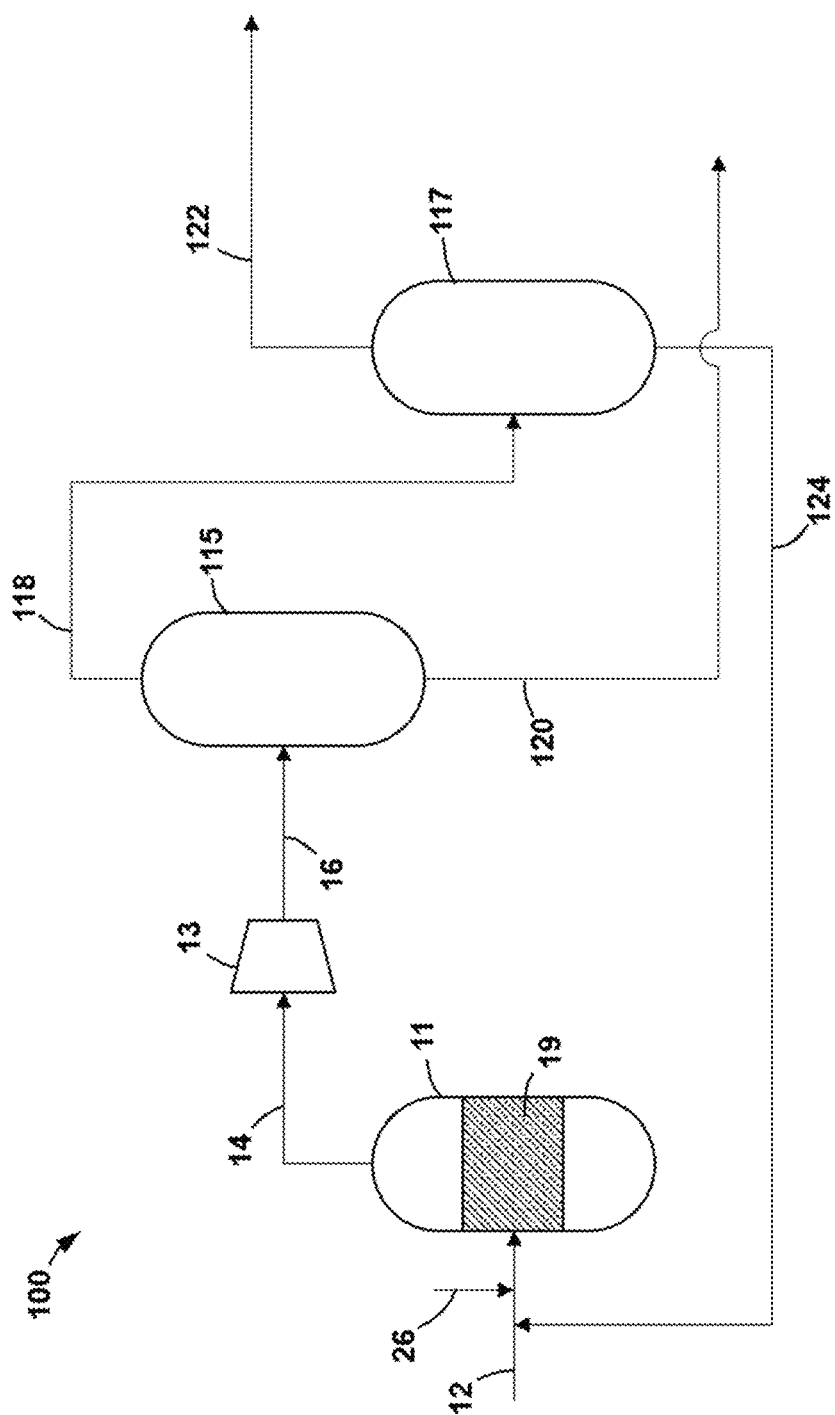
FIG. 2 is a flow diagram of another embodiment of a process for producing an aromatic hydrocarbon-containing product stream from an alkane-containing feedstock in accordance with a least some embodiments disclosed herein.

Referring now to FIG. 2, another embodiment of a process (shown and described as process 100) for producing an aromatic-rich product stream from a light alkane feedstock is shown. Process 100 is substantially similar to process 10, and thus, like numerals are utilized for like components, and the description below will focus on the elements and features of process 100 that are different from process 10.

In particular, in this embodiment, process 100 includes separation units 115 and 117 in place of separation units 15, 17, respectively. Specifically, reactor effluent stream 14 is first flowed from reactor 11 (optionally as a compressed stream 16 with the aid of the optional compressor 13) to separation unit 115, which may comprise a single or multiple separation reactors, columns, etc. In this embodiment separation unit 115 is configured to separate the reactor effluent stream 14 into a lights stream 118 comprising $C_1$-$C_6$ hydrocarbons and hydrogen gas ($H_2$), and a bottoms stream 120 comprising $C_{7+}$ hydrocarbons.

Like bottoms stream 24 in the embodiment of FIG. 1, bottoms stream 120 may include a substantial fraction of toluene and/or xylenes. As a result, stream 120 may be fed to another unit or process in order to facilitate the production and/or isolation of other valuable products, such as, for example, para-xylene. In particular, bottoms stream 120 may be provided to a para-xylene production unit (e.g., toluene methylation unit, crystallization, selective adsorption, or combinations thereof).

The lights stream 118 is routed to separation unit 117, which may also comprise a single or multiple separation reactors, columns, etc. In this embodiment separation unit 117 is configured to separate lights stream 118 into another lights stream 122 comprising methane ($CH_4$) and hydrogen ($H_2$), and a bottoms stream 124 comprising $C_2$-$C_6$ aromatic hydrocarbons. In at least some embodiments the bottoms stream 124 is similarly and/or identically configured (e.g., in composition, flow rate, etc.) to lights stream 22 previously described above and shown in FIG. 1. As shown in FIG. 2, bottoms stream 124 may be recycled back to reactor 11 in order to provide additional benzene into the fluids flowing into reactor chamber 11 and thereby decrease the resulting amount of net benzene produced in reactor 11 as previously described above. In addition, as is previously described above for the embodiment of FIG. 1, additional benzene may be provided to feed stream 12, either in addition to or in lieu of the benzene provided from bottoms stream 124, from additional stream 26 (being previously described above).

Particular reference will now be made to the following non-limiting example.

A Gallium-containing H-ZSM-5 catalyst was tested for the conversion of an ethane feed in the presence of various concentrations of benzene via a co-feed. The process conditions for this test included a temperature of 640° C., a weight hourly space velocity of 5 hr$^{-1}$ (ethane), and a pressure of 30 psia (ethane). FIG. 2 is a chart showing the noted the effect of the benzene co-feed concentration on product yields and ethane conversion. In particular, FIG. 2 shows the observed effect the changing benzene co-feed concentration had on the ethane conversion rate and the yields of Methane, Benzene, and $C_{7+}$ hydrocarbons. For convenience, the numeral data that is shown in FIG. 2 is also presented below in Table 1.

TABLE 1

| Benzene Co-Feed [wt. %] | Yield [wt. %; ethane basis] | | | Ethane Conversion [%] |
| --- | --- | --- | --- | --- |
| | Methane | Benzene (net) | $C_{7+}$ | |
| 0 | 5.2 | 7.4 | 11.9 | 31.2 |
| 4.8 | 4.4 | 3.9 | 12.8 | 27.9 |
| 9.1 | 3.5 | 1.5 | 13.2 | 25.2 |
| 20 | 3.2 | −3.8 | 16.1 | 22.7 |

Figure 3:
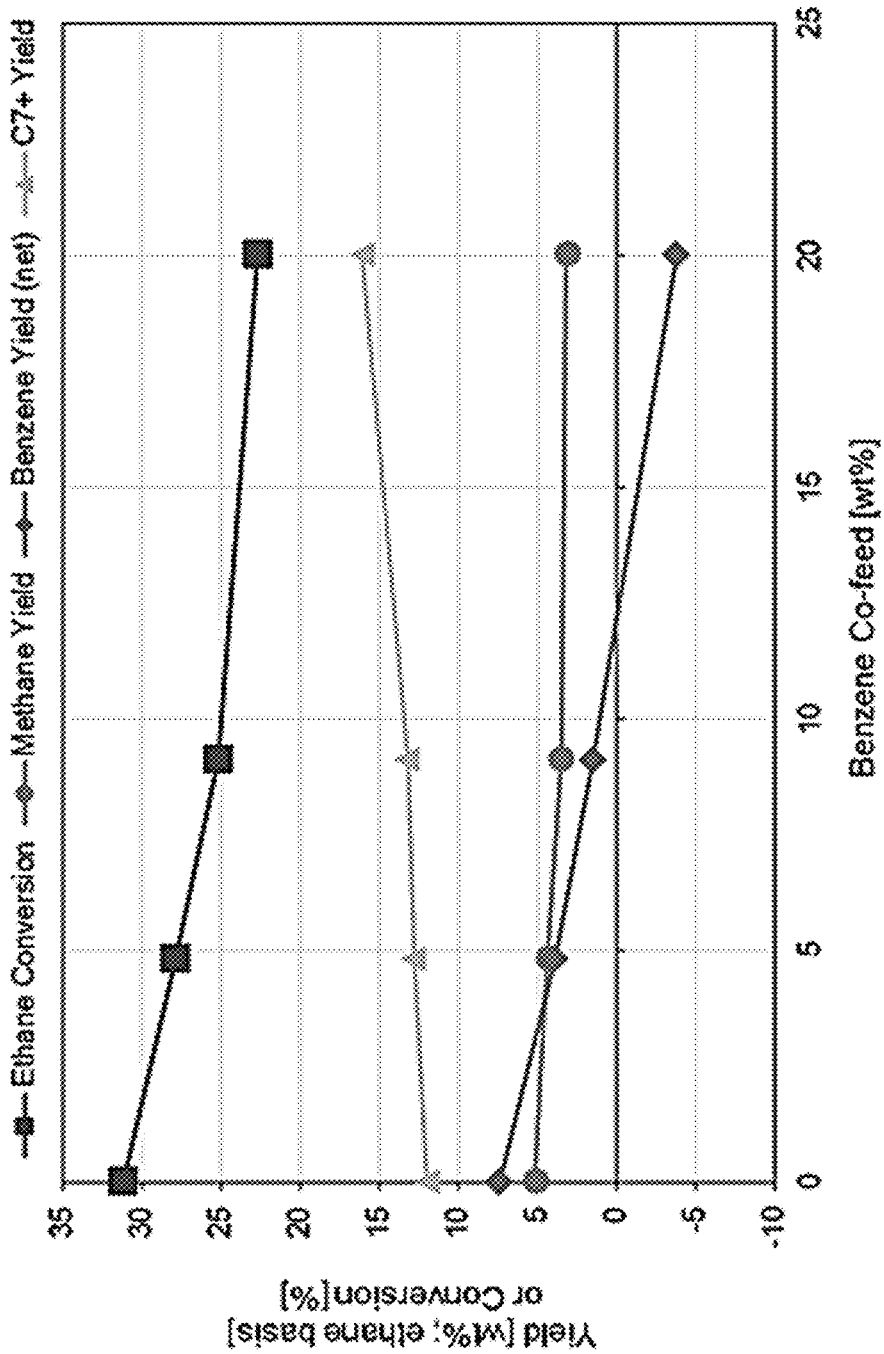
FIG. 3 is a chart showing the resulting yields from an aromatization catalyst being co-fed ethane and benzene in accordance with at least some of the embodiments disclosed herein.

As can been seen from both the chart in FIG. 3 and numerical data in Table 1 above, the net benzene yields decrease with increasing benzene concentration in the ethane feed with a zero net yield of benzene occurring between about 10 wt. % and 14 wt. % benzene in the feed. In addition, methane yields also decreased with increasing benzene concentration in the ethane feed. This suggests that benzene in the feed is not being converted to methane. Further, $C_{7+}$ hydrocarbon yields increased with increasing benzene concentration in the ethane feed. This suggests that a portion of the benzene in the feed was converted to products with larger carbon numbers (e.g., $C_{7+}$ aromatic hydrocarbons such as toluene, xylenes, etc.). Finally, it should be appreciated that the overall ethane conversion decreased with increasing benzene concentration in the ethane feed.

While various embodiments have been disclosed herein, modifications thereof can be made without departing from the scope or teachings herein. In particular, many variations and modifications of the systems, apparatus, and processes described herein are possible and are within the scope of the disclosed subject matter. Accordingly, embodiments disclosed herein are exemplary only and are not limiting. As a result, the scope of protection is not limited to the embodiments described herein, but is only limited by the claims that follow, the scope of which shall include all equivalents of the subject matter of the claims. Unless expressly stated otherwise, the steps in a method claim may be performed in any order. The use of identifiers such as (a), (b), (c) before steps in a method claim is not intended to and does not specify a particular order to the steps. Rather the use of such identifiers are used to simplify subsequent reference to such steps. Finally, the use of the term "including" in both the description and the claims is used in an open ended fashion, and should be interpreted as meaning "including, but not limited to."

The invention claimed is:

1. A process for producing C7+ aromatic hydrocarbons, the process comprising:
   a) providing an ethane-containing stream comprising at least 50 wt. % ethane based on a total weight of the ethane-containing stream;
   b) merging the ethane-containing stream with a benzene-containing stream to produce a merged stream comprising a first benzene content of at least 14 wt. % benzene and a first $C_{7+}$ aromatic content; and
   c) contacting the merged stream with an aromatization catalyst at a temperature in a range from about 640° C. to about 750° C. to produce an effluent stream comprising a second benzene content and a second $C_{7+}$ aromatic content,
   wherein the second benzene content is less than the first benzene content, and
   wherein the second $C_{7+}$ aromatic content is greater than the first $C_{7+}$ aromatic content.

2. The process of claim 1, further comprising separating at least some benzene from the effluent stream.

3. The process of claim 2, wherein the benzene-containing stream is provided from outside the process.

4. The process of claim 3, wherein the benzene-containing stream comprises greater than 50 wt. % benzene based on a total weight of the benzene-containing stream.

5. The process of claim 4, wherein the merged stream has 14 wt. % to about 30 wt. % benzene based on a total weight of the merged stream.

6. The process of claim 5, wherein the merged stream has about 14 wt. % to about 20 wt. % benzene based on the total weight of the merged stream.

7. The process of claim 6, further comprising:
   (c) separating a $C_{7+}$ aromatic hydrocarbon-containing stream from the effluent stream; and
   (d) providing the $C_{7+}$ aromatic hydrocarbon-containing stream to a para-xylene production unit.

8. The process of claim 7, wherein greater than 40%, by volume, of the ethane in the merged stream is converted into $C_{7+}$ aromatic hydrocarbons during the contacting in (c).

9. The process of claim 8, wherein greater than 90%, by volume, of the ethane in the merged stream is converted into $C_{7+}$ aromatic hydrocarbons during the contacting in (c).

10. The process of claim 9, wherein the aromatization catalyst comprises ZSM-5.

11. The process of claim 10, wherein the aromatization catalyst includes Gallium.

12. A process for producing $C_{7+}$ aromatic hydrocarbons, the process comprising:
    a) flowing a feed stream to an aromatization reactor, wherein the feed stream comprises a first benzene content of at least 14 wt. % and an ethane content of at least 50 wt. %, based on a total weight of the feed stream;
    b) contacting the feed stream with an aromatization catalyst at a temperature in a range from about 640° C. to about 750° C. to produce an effluent stream comprising a second benzene content and $C_{7+}$ aromatics;
    c) separating the effluent stream to obtain an aromatic-containing stream comprising benzene and $C_2$-$C_6$ hydrocarbons; and
    d) recycling the aromatic-containing stream to the aromatization reactor,
    wherein the second benzene content is less than the first benzene content.

13. The process of claim 12, wherein 14 wt. % to about 30 wt. % benzene is provided to the aromatization reactor, based on a total weight of the feed stream and the aromatic-containing stream.

14. The process of claim 13, wherein about 14 wt. % to about 20 wt. % benzene is provided to the aromatization reactor, based on a total weight of the feed stream and the aromatic-containing stream.

15. The process of claim 14, wherein greater than 40%, by volume, of the ethane in the feed stream is converted into $C_{7+}$ aromatic hydrocarbons during the contacting in (b).

16. The process of claim 15, wherein greater than 90%, by volume, of the ethane in the feed stream is converted into $C_{7+}$ aromatic hydrocarbons during the contacting in (b).

17. The process of claim 16, wherein the aromatization catalyst comprises ZSM-5.

* * * * *